| United States Patent [19] | [11] Patent Number: 4,803,074 |
| Yoshida et al. | [45] Date of Patent: Feb. 7, 1989 |

[54] FR-900848 SUBSTANCE AND PREPARATION THEREOF

[75] Inventors: Masaru Yoshida, Tsukuba; Koki Horikoshi, Tokyo, both of Japan

[73] Assignee: Fujisawa Pharmaceutical Co., Ltd., Osaka, Japan

[21] Appl. No.: 175,297

[22] Filed: Mar. 30, 1988

[30] Foreign Application Priority Data

Apr. 10, 1987 [GB] United Kingdom ............... 8708635

[51] Int. Cl.⁴ .................. A61K 35/74; C12P 1/06; C12P 1/04

[52] U.S. Cl. .................. 424/122; 435/169; 435/170

[58] Field of Search .............. 424/122; 435/170, 169

Primary Examiner—Jerome D. Goldberg
Attorney, Agent, or Firm—Oblon, Fisher, Spivak, McClelland & Maier

[57] ABSTRACT

This invention relates to a compound, FR-900848, having antimicrobial activity against various microorganisms, to a process for the preparation of same and to a pharmaceutical composition comprising same.

3 Claims, No Drawings

FR-900848 SUBSTANCE AND PREPARATION THEREOF

This invention relates to a new compound having a biological activity, hereinafter referred to as FR-900848 substance. More particularly, this invention relates to a new biologically active FR-900848 substance and its pharmaceutically acceptable salts, which have antimicrobial activity against various microorganisms, to a process for their preparation, and to pharmaceutical compositions comprising the same.

Accordingly, it is the object of this invention to provide a new FR-900848 substance and its pharmaceutically acceptable salts, which are active against various microorganisms, and useful for the treatment of infectious diseases in human beings and animals.

Suitable pharmaceutically acceptable salts of FR-900848 substance are conventional non-toxic salts and may include an acid addition salt such as an inorganic acid addition salt (e.g. hydrochloride, hydrobromide, sulfate, phosphate, etc.); an organic carboxylic or sulfonic acid additional sale (e.g. formate, acetate, trifluoroacetate, maleate, tartrate, methanesulfonate, benzenesulfonate, p-toluenesulfonate, etc.), a salt with a basic or acidic amino acid (e.g. arginine sale, aspartate, glutamate, etc.), or the like.

FR-900848 substance of this invention can be produced by fermentation of FR-900848 substance-producing strain belonging to the genus Streptoverticillium such as *Streptoverticillium fervens* HP891 in a nutrient medium.

The fermentation process is explained in detail in the following.

(i) Microorganism:

Particulars of the microorganism used for producing FR-900848 substance is explained in the following.

(a) Taxonomic studies on strain HP891:

Strain HP891 was isolated from a soil sample obtained from Tsukuba-shi, IBARAKI, JAPAN.

The methods described by Shirling and Gottlieb[*1] were employed for this taxonomic study. Morphological observations were made with light and electron microscopes from cultures grown at 30° C. for 21 days on oatmeal agar, glycerol-asparagine agar and sucrose-nitrate agar. Branching type of sporophores was verticillate and the form of mature sporophores was Monoverticillus with 3 to 10 spores in each chain. The spores were determined by electron microscopy to be cylindrical and measured 0.4–0.6×1.0–1.6 μm in size. Spore surfaces were smooth. Neither fragmentation of hyphae nor formation of spores occurred in the substrate mycelium. Sporangia, sclerotia and zoospores were not observed.

Cultural characteristics were observed on ten media described by Shirling and Gottlieb[*1] and Waksman[*2]. Incubation was carried out at 30° C. for 21 days. The color names used in this study were taken from Methuen Handbook of Colour.[*3] the aerial mass color belonged to red color series when grown on yeast-malt extract agar, inorganic salts-starch agar and oatmeal agar, Results are shown in Table 1.

[*1] Shirling, E. B. and D. Gottlieb: Methods for characterization of Streptomyces species: Intern. J. Syst. Bacteriol. 16: 313–340, 1966
[*2] Waksman, S. A.: The actinomycetes Vol. 2 Classification, identification and description of genera and species: The williams and Wilkins Co., Baltimore, 1961
[*3] Kornerup, A. and J. H. Wanscher: Methuen Handbook of Colour: Methuen, London, 1978

TABLE 1

Cultural characteristics of stain HP891

| Medium | Cultural characteristics | |
|---|---|---|
| yeast-malt extract agar | growth: | good |
| | aerial mass color: | pale red, dull red |
| | reverse side color: | red, violet brown |
| | soluble pigment: | none |
| oatmeal agar | growth: | moderate |
| | aerial mass color: | brownish red |
| | reverse side color: | brownish red |
| | soluble pigment: | none |
| inorganic salts-starch agar | growth: | good |
| | aerial mass color: | pale red |
| | reverse side color: | red |
| | soluble pigment: | none |
| glycerin-asparagine agar | growth: | moderate |
| | aerial mass color: | reddish white |
| | reverse side color: | postal red |
| | soluble pigment: | none |
| peptone-yeast extract-iron agar | growth: | good |
| | aerial mass color: | none |
| | reverse side color: | orange gray |
| | soluble pigment: | none |
| tyrosine agar | growth: | moderate |
| | aerial mass color: | pale red |
| | reverse side color: | grayish red |
| | soluble pigment: | none |
| glucose-asparagine agar | growth: | good |
| | aerial mass color: | pale red |
| | reverse side color: | red |
| | soluble pigment: | none |
| nutrient agar | growth: | moderate |
| | aerial mass color: | none |
| | reverse side color: | dark blond |
| | soluble pigment: | none |
| Bennet agar | growth: | good |
| | aerial mass color: | pale red, white |
| | reverse side color: | red, violet brown |
| | soluble pigment: | none |
| sucrose-nitrate agar | growth: | poor |
| | aerial mass color: | reddish white, white |
| | reverse side color: | reddish white |
| | soluble pigment: | none |

Wall analysis was performed by the methods of Becker et al.[*4] and Yamaguchi[*5]. Analysis of whole cell hydrolysates showed the presence of LL-diaminopimeric acid. Accordingly, the cell wall of this strain is classified as type I.

[*4] Becker, B., M. P. Lechevalier, R. E. Gordon and H. A. Lechevalier: Rapid differentiation between Nocardia and Streptomyces by paper chromatography of whole-cell hydrolysates: Appl. Microbiol. 12, 421–423, 1964
[*5] Yamaguchi, T.: Comparison of the cell-wall composition of morphologically distinct actinomycetes: J. Bacteriol. 89, 444–453, 1965

Physiological properties of strain HP891 were as follows.

Temperature range for growth was determined on yeast-malt extract agar using a temperature gradient incubator (Toyo Kagaku Sangyo Co., Ltd.). Summarized physiological properties of strain HP891 are shown in Table 2. Temperature range for growth was from 10° C. to 40° C. with optimum temperature of 32° C. Milk peptonization and coagulation were positive. Production of melanoid pigment was positive on peptone-yeast extract-iron agar.

TABLE 2

Physiological properties of stain HP891

| Conditions | Characteristics |
|---|---|
| temperature range for growth | 10° C.–40° C. |
| optimum temperature for growth | 32° C. |
| gelatin liquefaction | negative |
| milk coagulation | positive |
| milk peptonization | positive |
| starch hydrolysis | positive |
| production of melanoid pigment | positive |

TABLE 2-continued

| Physiological properties of stain HP891 | |
|---|---|
| Conditions | Characteristics |
| decomposition of cellulose | negative |

Utilization of carbon sources was examined according to the method of Pridham and Gottlieb[*6]. The results were determined after 14 days incubation at 30° C. This strain could utilize D-glucose, D-fructose and inositol. Results are shown in Table 3.

[*6] Pridham, T. G. and D. Gottlieb: The utilization of carbon compounds by some Actinomycetales as an aid for species determination: J. Bacteriol. 56: 107-114, 1948

TABLE 3

| Carbon utilization of strain HP891 | |
|---|---|
| Compounds | Growth |
| D-glucose | + |
| Sucrose | − |
| D-xylose | − |
| D-fructose | + |
| L-ramnose | − |
| raffinose | − |
| L-arabinose | − |
| inositol | + |
| mannitol | − |

+: utilization
−: no utilization

Microscopic studies and cell wall analysis of strain HP891 indicate that this stain belongs to the genus Streptoverticillium. After a comparison of this strain was made with the published description[*7], [*8], [*9], [*10], [*11] of various Streptoverticillium species, the characteristics of stain HP891 proved to resemble that of *Streptoverticillium fervens*. As a result of more precise comparison between stain HP891 and *Streptoverticillium fervens* IFO 13343, strain HP891 was identified as a strain of *Streptoverticillium fervens*, and was designated as *Streptoverticillium fervens* HP891.

[*7] Buchanan, R. E. and N. E. Gibbons: Bergey's manual of determinative bacteriology, eight edition: The Williams and Wilkins Co., Baltimore, 1974
[*8] Shirling, E. B. and D. Gottlieb: Cooperative description of type culture of Streptomyces: 2. Species descriptions from first study: Intern. J. Syst. Bacteriol. 18: 69–189, 1968
[*9] Shirling, E. B. and D. Gottlieb: Cooperative description of type culture of Streptomyces: 3. Additional species descriptions from first and second studies: Intern. J. Syst. Bacteriol. 18: 279–392, 1968
[*10] Shirling, E. B. and D. Gottlieb: Cooperative description of type culture of Streptomyces: 4. Species descriptions from the second, third and forth studies: Intern. J. Syst. Bacteriol. 19: 391–512, 1969
[*11] Locci, R., E. Baldacci and B. Petrolini: The genus Streptoverticillium A taxonomic study: Giorn. Microbiol. 17: 1–60, 1969

A culture of *Streptoverticillium fervens* HP891 has been deposited with Fermentation Research Institute Agency of Industrial Science and Technology (1-3, Higashi 1 chome Tsukuba-shi, IBARAKI, 305 JAPAN) on Mar. 31, 1987 under the number of FERM P-9310, and then said culture was transferred to Budapest Treaty route of the same depository on Mar. 18, 1988 under the new deposit number of FERM BP-1805.

(ii) Production of FR-900848 substance

FR-900848 substance of this invention is produced when a FR-900848 substance-producing strain belonging to the genus Streptoverticillium (e.g. *Streptoverticillium fervens* HP891) is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, starch, fructose or glycerin.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea or amino acid.

The carbon and nitrogen sources, though advantageously employed in combination, need not to be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, or cobalt salts.

If necessary, especially when the culture medium foams seriously a defoaming agent, such as liquid paraffin, fatty oil, plant oil, mineral oil or silicone may be added.

As in the case of the preferred methods used for the production of other biologically active substances in massive amounts, submerged aerobic cultural conditions are preferred for the production of FR-900848 substance in massive amounts.

For the production in small amounts, a shaking or surface culture in a flask or bottle is employed.

Further, when the growth is carried out in large tanks, it is preferable to use the vegetative form of the organism for inoculation in the production tanks in order to avoid growth lag in the process of production of FR-900848 substance. Accordingly, it is desirable first to produce a vegetative inoculum of the organism by inoculating a relatively small quantity of culture medium with spores or myceria of the organism and culturing said inoculated medium, and then to transfer the cultured vegetative inoculum to large tanks. The medium, in which the vegetative inoculum is produced, is substantially the same as or different from the medium utilized for the production of FR-900848 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 10° C. and 40° C., preferably 25° C. to 35° C., for a period of about 50 hours to 100 hours, wich may be varied according to fermentation conditions and scales.

When the fermentation is completed, the culture broth is then subjected for recovery of FR-900848 substance to various procedures conventionally used for recovery and purification of biological active substances, for instance, solvent extraction with an appropriate solvent or a mixture of some solvents, chromatography or recrystallization from an appropriate solvent or a mixture of some solvents.

According to this invention, in general, FR-900848 substance is found mainly in the cultured mycelia. Accordingly, the culture broth is separated by means of filtration or centrifuging to remove the mycelia, and then FR-900848 substance is removed from the mycelia by means of extraction using an appropriate organic solvent such as acetone or ethyl acetate, or a mixture of these solvents.

The extract is treated by a conventional manner to provide FR-900848 substance, for example, the extract is concentrated by evaporation or distillation to a smaller amount and the resulting residue containing active material, i.e. FR-900848 substance is purified by conventional purification procedures, for example, chromatography or recrystallization from an appropriate solvent or a mixture of some solvents.

(iii) Physico-chemical properties of FR-900848 substance

FR-900848 substance as obtained according to the aforementioned fermentation process has the following physico-chemical properties.

Appearance: colorless needles.
Nature: acidic.
Melting point: 198°-201° C. (dec).
Specific rotation: $[\alpha]_D^{20}$: $-36.22°$ (c=0.5, DMSO).
Molecular formula: $C_{32}H_{43}N_3O_6$.
Elemental Analysis: Calcd: for $C_{32}H_{43}N_3O_6$: C, 67.94; H, 7.60; N, 7.43; O, 16.97 (%); Found: C, 68.57; H, 7.51; N, 7.53; (O, 16.39) (%).
Molecular wieght: FAB-MS m/z 565.
Solubility: soluble: dimethylsulfoxide; slightly soluble: methanol, ethyl acetate, chloroform; insoluble: water.
Color reaction: positive: Dragendorff reaction, Ehrlich reaction, cerium sulfate reaction, iodine vapor reaction; negative: Ninhydrin reaction, ferric chloride reaction, Molish reaction.
Thin layer chromatography: Rf value (silica plate, Kieselgel 60 $F_{254}$, made by Merck & Co., Inc.): 0.55 (chloroform:methanol=5:1); 0.70 (chloroform:methanol included 10% acetic acid=5:1).
High pressure thin layer chromatography: Rf value (RP-18 $F_{254}$, made by Merck & Co., Inc.): 0.21 (methanol:10% acetic acid=9:1).
High pressure liquid column chromatography (HPLC): (Column YMC-Pack A-302 (5 μm, 4.5×150 mm) (made by Yamamura Chemical Institute) HITACHI M655 HPLC Processor (detect UV 280 nm) solvent system methanol:10% acetic acid=9:1) retention time: 4.42 minutes.
Ultraviolet absorption spectrum: $\lambda_{max}^{methanol}=280$ nm ($\epsilon=31,000$); $\lambda_{max}^{0.1N\ HCl-methanol}=280$ nm ($\epsilon=31,000$); $\lambda_{max}^{0.1N\ NaCl-methanol}=280$ nm ($\epsilon=31,000$).
Infrared absorption spectrum: $\nu_{max}^{Nujol}=3320$, 3250, 3055, 3000(sh), 2950(sh), 2920, 2850, 1760, 1708, 1675, 1650, 1615, 1540, 1520(sh), 1480, 1455, 1410, 1395, 1370, 1350, 1330, 1308, 1270, 1245, 1230, 1202, 1180, 1160, 1133, 1120(sh), 1093, 1068, 1030, 1020, 986, 955(sh), 945, 928, 917, 900, 880, 860, 850(sh), 825, 800, 760, 740, 720 $cm^{-1}$.

$^1$H Nuclear magnetic resonance spectrum: (DMSO-$d_6$, 400.13 MHz) δ: 0.01-0.15 (4H, m), 0.29-0.37 (3H, m), 0.39-0.45 (1H, m), 0.46-0.76 (8H, m), 0.92-1.06 (3H, m), 0.99 (3H, d, J=6 Hz), 1.25 (1H, m), 2.43-2.60 (2H, m), 3.21 (1H, m), 3.26-3.44 (3H, m), 3.69 (1H, m), 3.75 (1H, m), 3.94 (1H, m), 4.91-5.00 (2H, m), 5.02 (1H, d, J=4.9 Hz), 5.12 (1H, d, J=5.6 Hz), 5.64 (1H, dd, J=14.9 and 9.4 Hz), 5.66 (1H, d, J=6.0 Hz), 5.89 (1H, d, J=15.0 Hz), 6.20 (1H, dd, J=14.9 and 11.1 Hz), 6.94 (1H, dd, J=15.0 and 11.1 Hz), 8.02 (1H, t, J=5.7 Hz), 10.27 (1H, broad s) ppm.

$^{13}$C Nuclear magnetic resonance spectrum: (DMSO-$d_6$, 100.62 Hz) δ: 7.60(t), 7.65(t), 11.16(t), 12.95(t), 14.08(d), 14.37(t), 17.65(d), 17.81(d), 18.02(d), 18.29(d), 18.31(q), 19.67(d), 21.00(d), 21.24(d), 22.01(d), 23.28(d), 30.82(t), 35.97(t), 41.031(t), 70.06(d), 71.18(d), 81.21(d), 87.64(d), 121.45(d), 125.48(d), 130.27(d), 130.622(d), 139.44(d), 145.70(d), 153.10(s), 165.60(s), 170.29(s) ppm.

FR-900848 substance can be transferred to its suitable pharmaceutically acceptable salts by a conventional manner.

Biological properties of FR-900848 substance

As examples for showing biological activity of FR-900848 substance some biological data are explained in the following.

Test 1

MIC (minimal inhibitory concentration)
Test method:
In vitro antimicrobial activity was determined by the two-fold agar-plate dilution method as described below.
One loopful of an overnight culture of each test strain in malt extract broth was streaked on malt extract agar containing graded concentrations of FR-900848 substance and MIC was determined after incubation at 37° C. for 20 hours.
FR-900848 substance showed antimicrobial activity against fungi, for example, *Aspergillus niger*, *Geotrichum candidum*, *Trichophyton asteroides* and the like as described in Table 4.

TABLE 4

| MIC of FR-900848 substance | |
|---|---|
| Test organism | MIC (μg/ml) |
| *Aspergillus niger* IFO 4417 | 0.015 |
| *Geotrichum candidum* | 0.12 |
| *Aureobasidium pullulans* | 0.03 |
| *Mucor rouxianus* (Calmette) Wehmer | 0.03 |
| *Trichophyton asteroides* | 0.5 |
| *Fusarium oxysporum* | 0.05 |
| *Sclerotinia arachidis* | 0.05 |

Test 2

Acute toxicity of FR-900848 substance
Acute toxicity of FR-900848 substance in mice (ICR, male, 4 weeks old) by intraperitoneal injection is more than 1.0 g/kg.
From the test results, it is realized that FR-900848 substance has an anti-microbial activity.
The pharmaceutical composition of this invention can be used in the form of a pharmaceutical preparation, for example, in solid, semisolid or liquid form, which contains FR-900848 substance or its pharmaceutically acceptable salts, as an active ingredient in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. And, if necessary, in addition, auxiliary, stabilizing, thickening and coloring agents and perfumes may be used. FR-900848 substance is included in the pharmaceutical composition in an amount sufficient to produce the desired antimicrobial effect upon the process or condition of diseases.
For applying the composition to human, it is preferable to apply it by intravenous, intramuscular or oral administration. While the dosage of therapeutically effective amount of FR-900848 substance varies from and also depends upon the age and condition of each individual patient to be treated, in the case of intravenous administration, a daily dose of 0.01-1 mg of FR- 900848 substance per kg weight of human being, in the case of intramuscular administration, a daily dose of 0.1–10 mg of FR-900848 substance per kg weight of human being, in case of oral administration, a daily dose of 0.5–50 mg of FR-900848 substance per kg weight of human being is generally given for treating infectious disease.

The following examples are given for the purpose of illustrating the present invention in more detail.

EXAMPLE

Fermentation:

An aqueous seed medium (160 ml) containing corn starch (1%), glycerin (1%), glucose (0.5%), cotton seed meal (1%), dried yeast (0.5%), corn steep liquor (0.5%) and calcium carbonate (0.2%) (adjusted to pH 6.5) was poured into each of 500 ml Erlenmeyer flasks and sterilized at 120° C. for 30 minutes. A loopful of *Streptoverticillium fervens* HP891 on matured slant culture was inoculated to the seed medium. The flasks were shaken on a rotary shaker (220 rpm, 5.1 cm throw) at 30° C. for 4 days. An aqueous production medium (180 liters) containing modified starch (4%), corn starch (1%), cotton seed meal (0.5%), dried yeast (0.5%), gluten meal (1%), $MgSO_4.7H_2O$ (0.1%), $KH_2PO_4$ (2%), $Na_2HPO_4.12H_2O$ (1.5%), Adekanol LG109 (deforming agent, trade mark, made by Asahi Denka Kogyo Co.) (0.05%) and Silicon KM-70 (deforming agent, trade mark, made by Shin-Etsu Chemical Co.) (0.05%) was poured into a 200-liter jar-fermentor, which has been sterilized at 120° C. for 30 minutes in advance. The resultant seed culture broth (3600 ml) was inoculated to a production medium and cultured at 30° C. for 5 days under aeration of 150 liters/minute and agitation of 300 rpm.

Isolation and purification:

The culture broth (175 liters) thus obtained was filtered with an aid of filter aid (Radiorite 600, trade mark, made by Showa Chemical Industry (5 kg). The mycelia cake was extracted with acetone (150 liters), yielding 50 liters of the extract, The acetone extract from mycelium was concentrated to 18 liters aqueous solution under reduced pressure at 20° C. The concentrate was extracted with ethyl acetate three times (total 50 liters). The extract was evaporated under reduced pressure at 20° C., The residue was dissolved in 75% aqueous methanol (500 ml), and passed through the column of reverse phase silica gel [YMC GEL $C_{18}$ (60–200 mesh), trade mark, made by Yamamura Chemical Institute, 1.5 liters]. The column was washed with 75% aqueous methanol (6 liters) and 80% aqueous methanol (4 liters), and then eluted was 90% aqueous methanol (2 liters). The eluate was evaporated under reduced pressure at 20° C. The residue was dissolved in methanol. After standing overnight at 4° C., the precipitated crystals were collected by filtration, washed with cooled methanol, and then dried under reduced pressure. Recrystallization from methanol gave colorless needle crystal of FR-900848 substance (328 mg).

What we claim is:

1. FR-900848 substance, wherein FR-900848 substance has following physico-chemical properties:
   Appearance: colorless needles
   Nature: acidic
   Melting point: 198°–201° C. (dec)
   Specific rotation: $[\alpha]_D^{20}$: $-36.22°$ (c=0.5, DMSO)
   Molecular formula: $C_{32}H_{43}N_3O_6$
   Elemental Analysis: Calcd: for $C_{32}H_{43}N_3O_6$: C, 67.94, H, 7.60, N, 7.43; O, 16.97 (%); Found: C, 68.57; H, 7.51; N, 7.53; (O, 16.39) (%)
   Molecular weight: FAB-MS m/z 56
   Solubility:
      soluble: dimethylsulfoxide;
      slightly soluble: methanol, ethyl acetate, chloroform;
      insoluble: water
   Color reaction:
      positive: Dragendorff reaction, Ehrlich reaction, cerium sulfate reaction, iodine vapor reaction
      negative: Ninhydrin reaction, ferric chloride reaction, Molish reaction
   Thin layer chromatography:
      Rf value (silica plate, Kieselgel 60 $F_{254}$, made by Merck & Co., Inc.):
      0.55 (chloroform:methanol=5:1);
      0.70 (chloroform:methanol included 10% acetic acid=5:1)
   High pressure thin layer chromatography:
      Rf value (RP-18 $F_{254}$, made by Merck & Co., Inc.): 0.21 (methanol:10% acetic acid=9:1)
   High pressure liquid column chromatography (HPLC): (Column YMC-Pack A-302 (5 μm, 4.5×150 mm) (made by Yamamura Chemical Institute)
      HITACHI M655 HPLC Processor (detect UV 280 nm);
      solvent system methanol:10% acetic acid=9:1); retention time: 4.42 minutes
   Ultraviolet absorption spectrum:
      $\lambda_{max}^{methanol}=280$ nm ($\epsilon=31,000$);
      $\lambda_{max}^{0.1N\ HCl-methanol}=280$ nm ($\epsilon=31,000$);
      $\lambda_{max}^{0.1N\ NaCl-methanol}=280$ nm ($\epsilon=31,000$)
   Infrared absorption spectrum: $\nu_{max}^{Nujol}=$ 3320, 3250, 3055, 3000(sh), 2950(sh), 2920, 2850, 1760, 1708, 1675, 1650, 1615, 1540, 1520(sh), 1480, 1455, 1410, 1395, 1370, 1350, 1330, 1308, 1270, 1245, 1230, 1202, 1180, 1160, 1133, 1120(sh), 1093, 1068, 1030, 1020, 986, 955(sh), 945, 928, 917, 900, 880, 860, 850(sh), 825, 800, 760, 740, 720 cm$^{-1}$
   $^1$H Nuclear magnetic resonance spectrum: (DMSO-$d_6$, 400.13 MHz); δ: 0.01–0.15 (4H, m), 0.29–0.37 (3H, m), 0.39–0.45 (1H, m), 0.46–0.76 (8H, m), 0.92–1.06 (3H, m), 0.99 (3H, d, J=6 Hz), 1.25 (1H, m), 2.43–2.60 (2H, m), 3.21 (1H, m), 3.26–3.44 (3H, m), 3.69 (1H, m), 3.75 (1H, m), 3.94 (1H, m), 4.91–5.00 (2H, m), 5.02 (1H, d, J=4.9 Hz), 5.12 (1H, d, J=5.6 Hz), 5.64 (1H, dd, J=14.9 and 9.4 Hz), 5.66 (1H, d, J=6.0 Hz), 5.89 (1H, d, J=15.0 Hz), 6.20 (1H, dd, J=14.9 and 11.1 Hz), 6.94 (1H, dd, J=15.0 and 11.1 Hz), 8.02 (1H, t, J=5.7 Hz), 10.27 (1H, broad s) ppm
   $^{13}$C Nuclear magnetic resonance spectrum: (DMSO-$d_6$, 100.62 Hz); δ: 7.60(t), 7.65(t), 11.16(t), 12.95(t), 14.08(d), 14.37(t), 17.65(d), 17.81(d), 18.02(d), 18.29(d), 18.31(q), 19.67(d), 21.00(d), 21.24(d), 22.01(d), 23.28(d), 30.82(t), 35.97(t), 41.031(t), 70.06(d), 71.18(d), 81.21(d), 87.64(d), 121.45(d), 125.48(d), 130.27(d), 130.622(d), 139.44(d), 145.70(d), 153.10(s), 165.60(s), 170.29(s) ppm.

2. A process for the production of FR-900848 substance as defined in claim 1, which comprises culturing *Streptoverticillium fervens* HP891 (FERM BP-1805), which is capable of producing FR-900848 substance, in an aqueous nutrient medium under aerobic conditions until substantial antimicrobial activity is imparted to the culture, and recovering FR-900848 substance.

3. An antimicrobial pharmaceutical composition which comprises an effective amount of an active ingredient FR-900848 substance as defined in claim 1, and a non-toxic, pharmaceutically acceptable carrier.

* * * * *